United States Patent [19]

Anaise

[11] Patent Number: 4,723,939
[45] Date of Patent: Feb. 9, 1988

[54] APPARATUS AND METHOD FOR MULTIPLE ORGAN PROCUREMENT

[75] Inventor: David Anaise, Dix Hills, N.Y.

[73] Assignee: The Research Foundation of State Univ. of New York, Albany, N.Y.

[21] Appl. No.: 892,192

[22] Filed: Jul. 31, 1986

[51] Int. Cl.[4] .................... A61F 7/12; A61M 29/00
[52] U.S. Cl. ................................. 604/113; 604/96
[58] Field of Search ............... 604/93, 96, 102, 113, 604/4, 27, 28, 101; 27/1, 21, 22 R, 24 R

[56] References Cited

U.S. PATENT DOCUMENTS 4,655,746 4/1987 Daniels et al. .................. 604/101

OTHER PUBLICATIONS

Organ Procurement II, Proceedings of the Second International Congress on Organ Procurement, Oct. 3–5, 1985, Detroit, Mich., pp. 28–30, (1986).

Primary Examiner—C. Fred Rosenbaum
Assistant Examiner—Gene B. Kartchner
Attorney, Agent, or Firm—Hoffmann & Baron

[57] ABSTRACT

In situ preservation of animal organs for transplantation is effected by establishing upper and lower blockages in a vascular conduit connected with such organs and then introducing a flushing solution into the conduit through a cannula at a flow rate sufficient to provide a renal flush of about 60 to 70 cc/100 g/min and until the core temperature of the organs being removed has been lowered to at least about 22° C. A particular cannula assembly and flushing kit also is provided.

31 Claims, 10 Drawing Figures

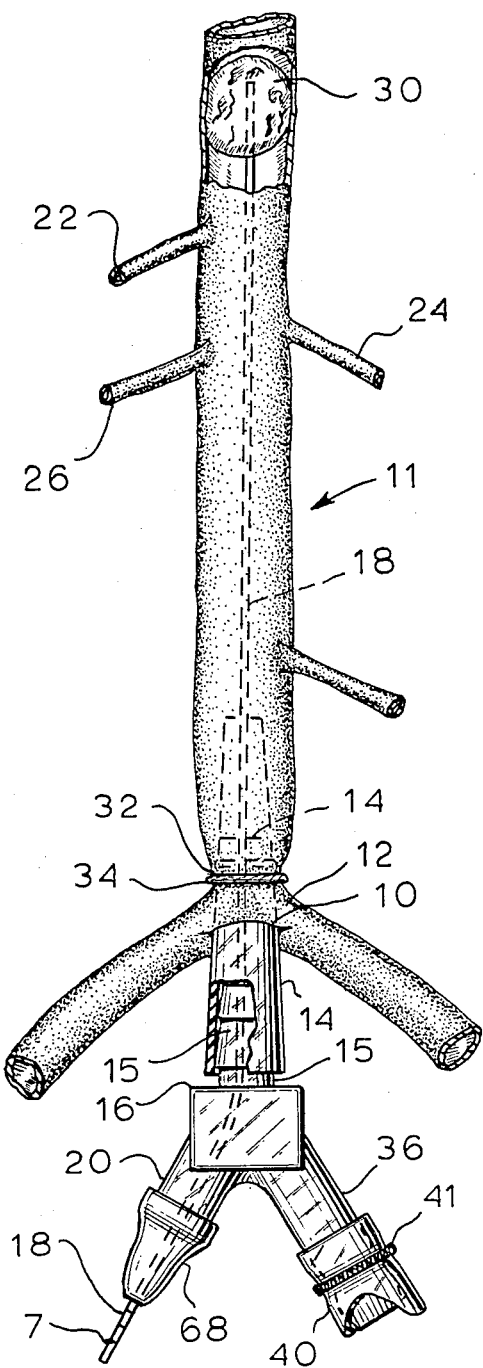
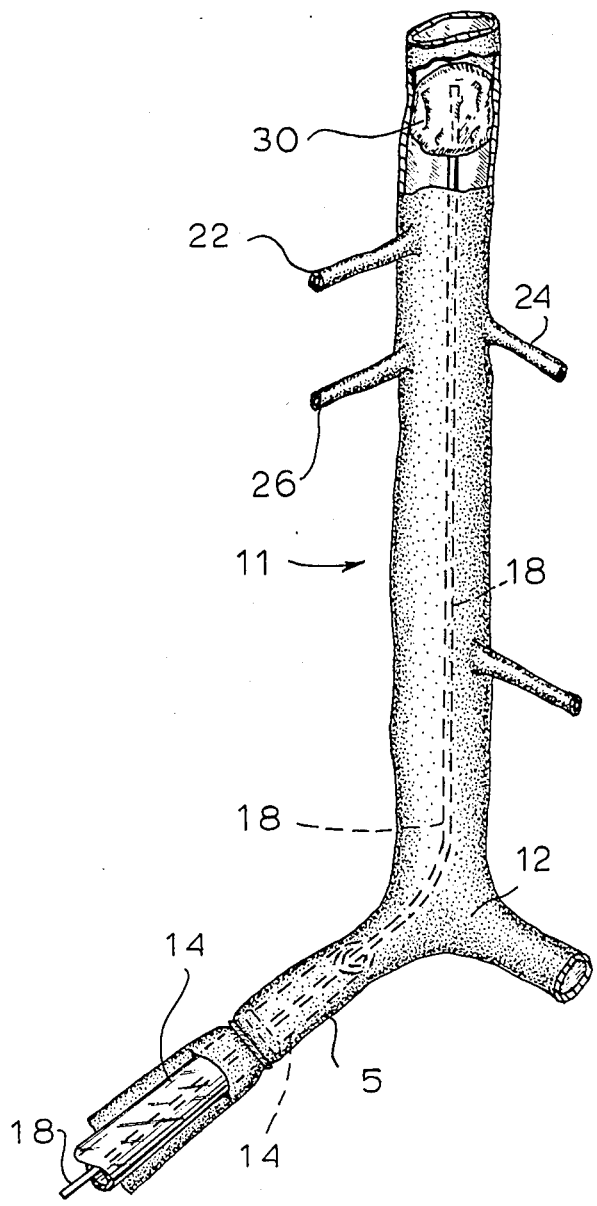
Fig. 1A
Fig. 1B

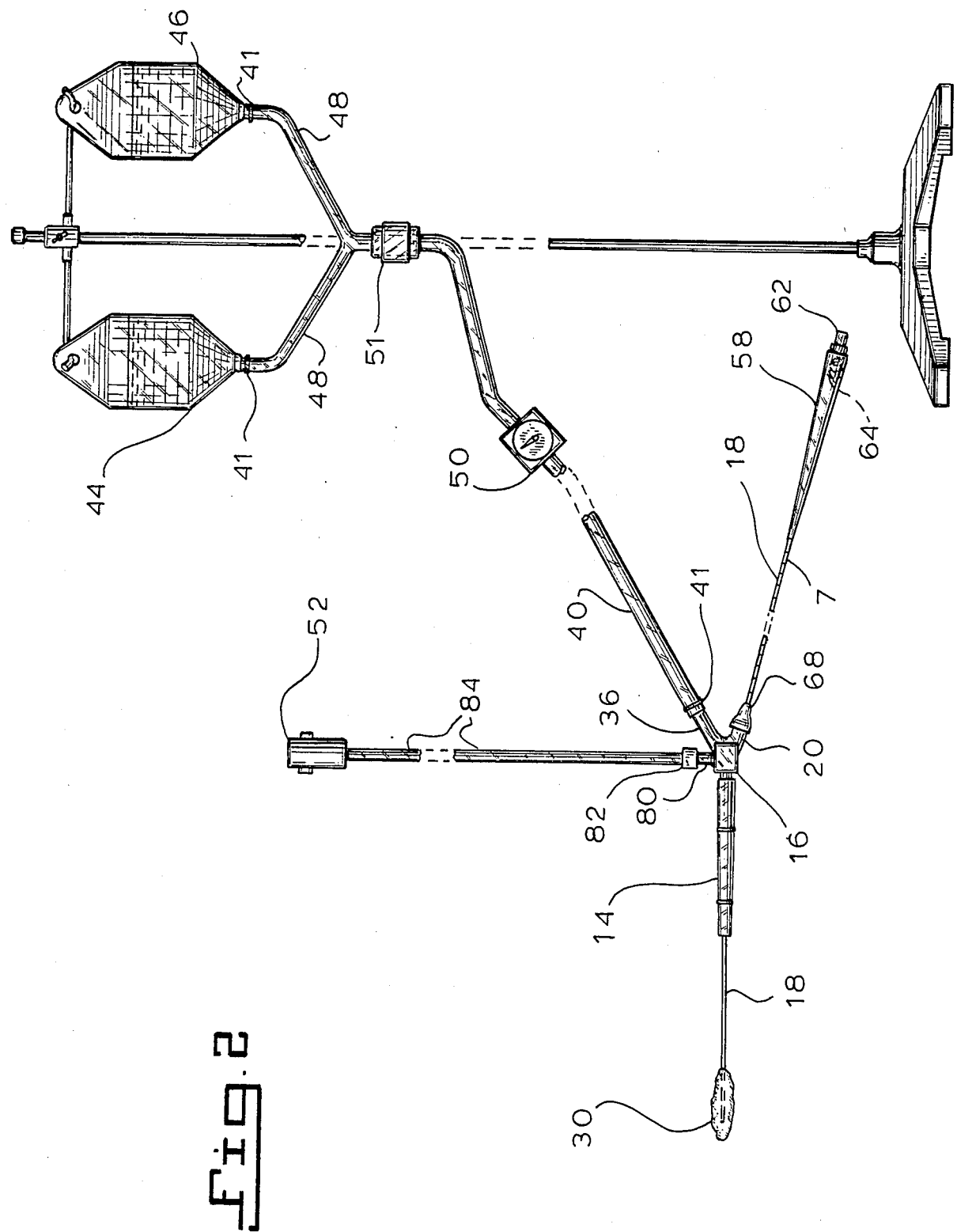

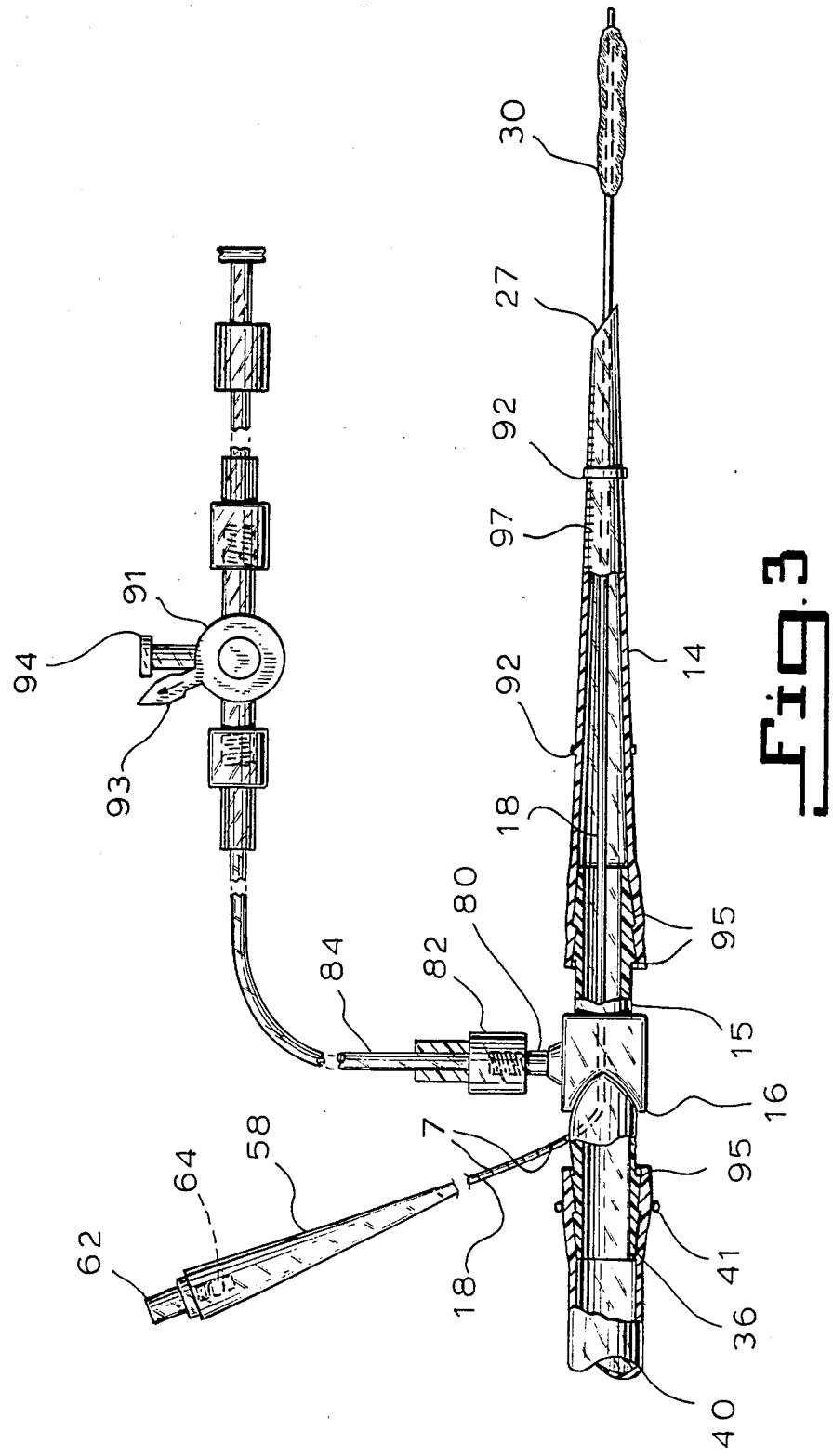

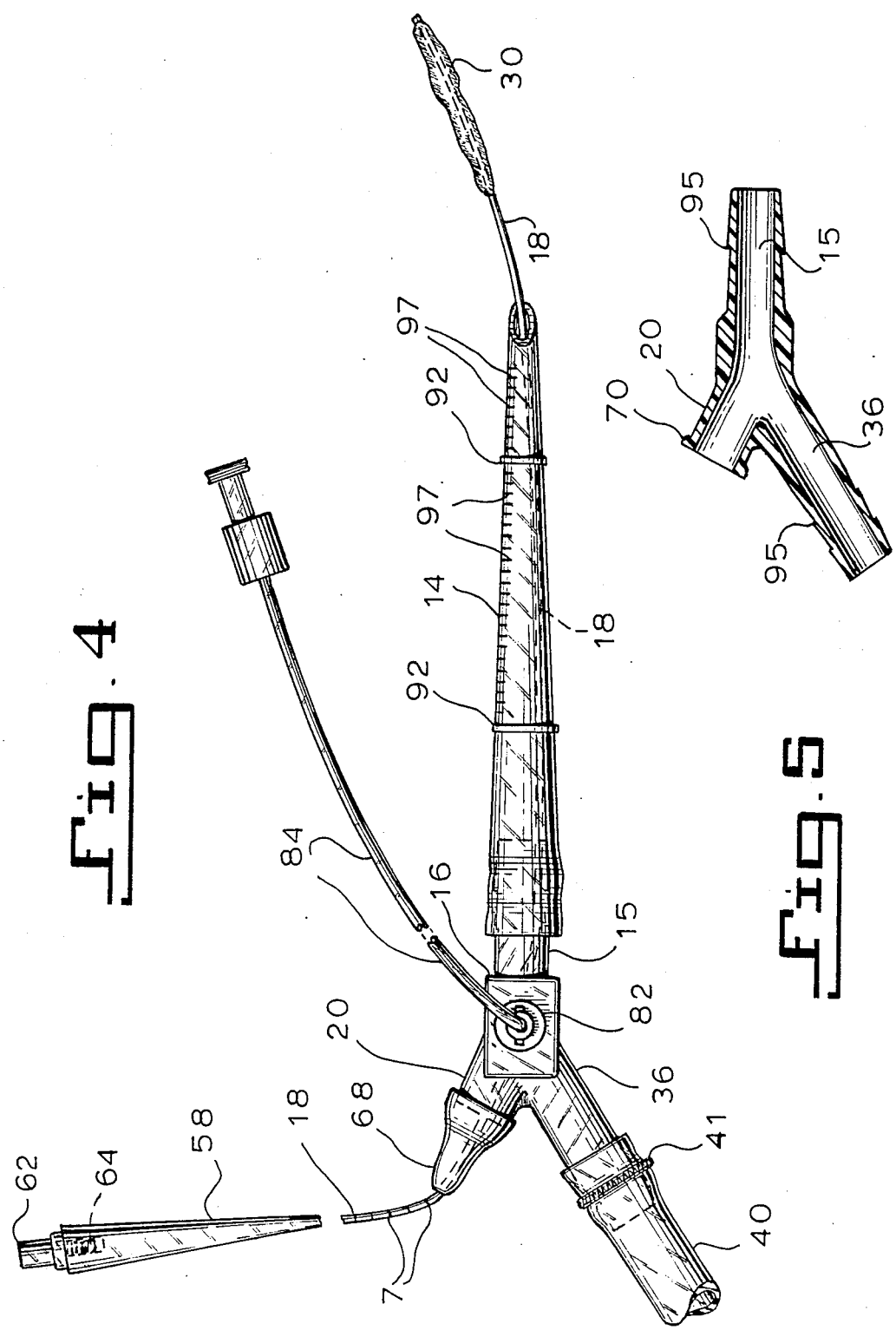

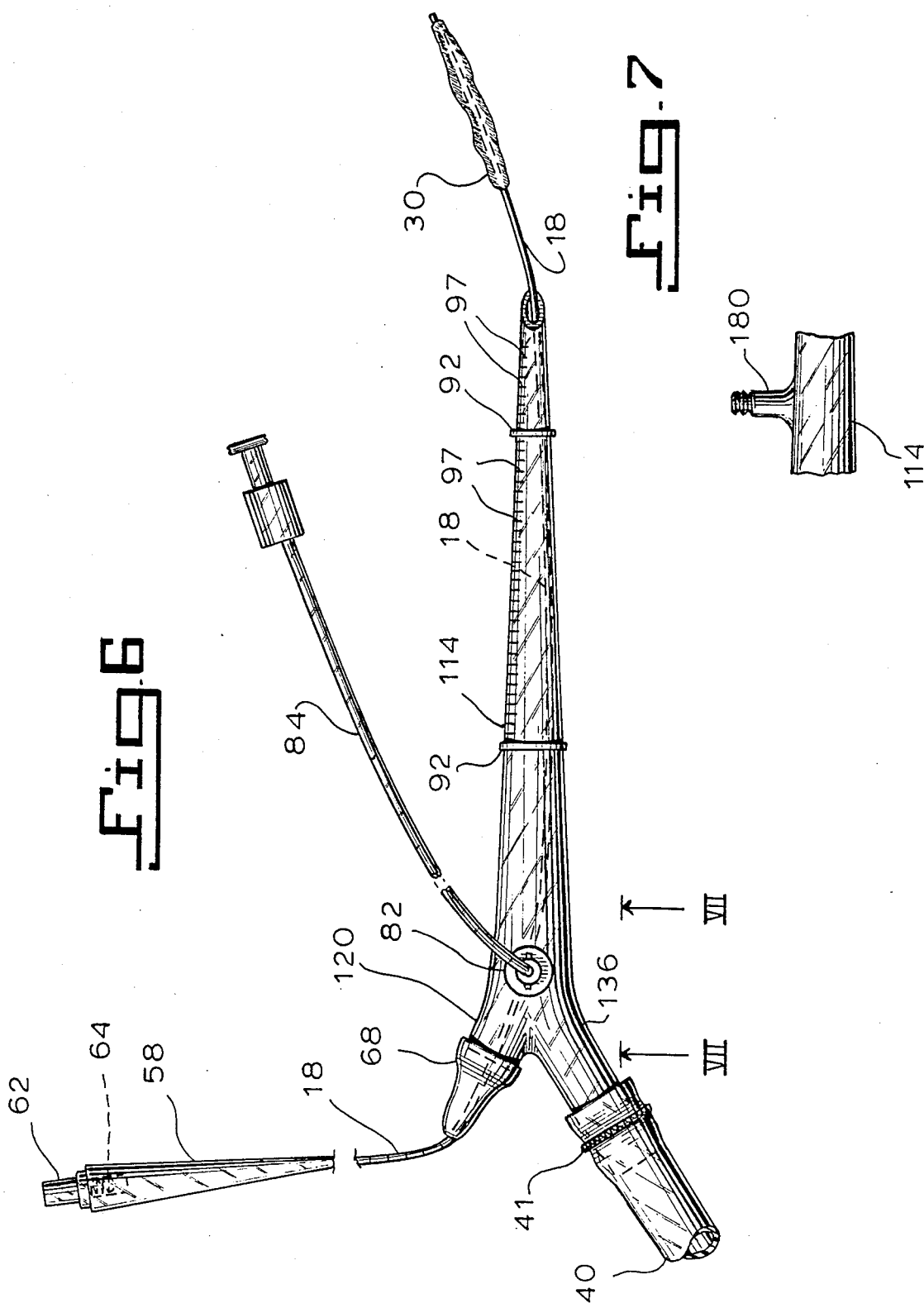

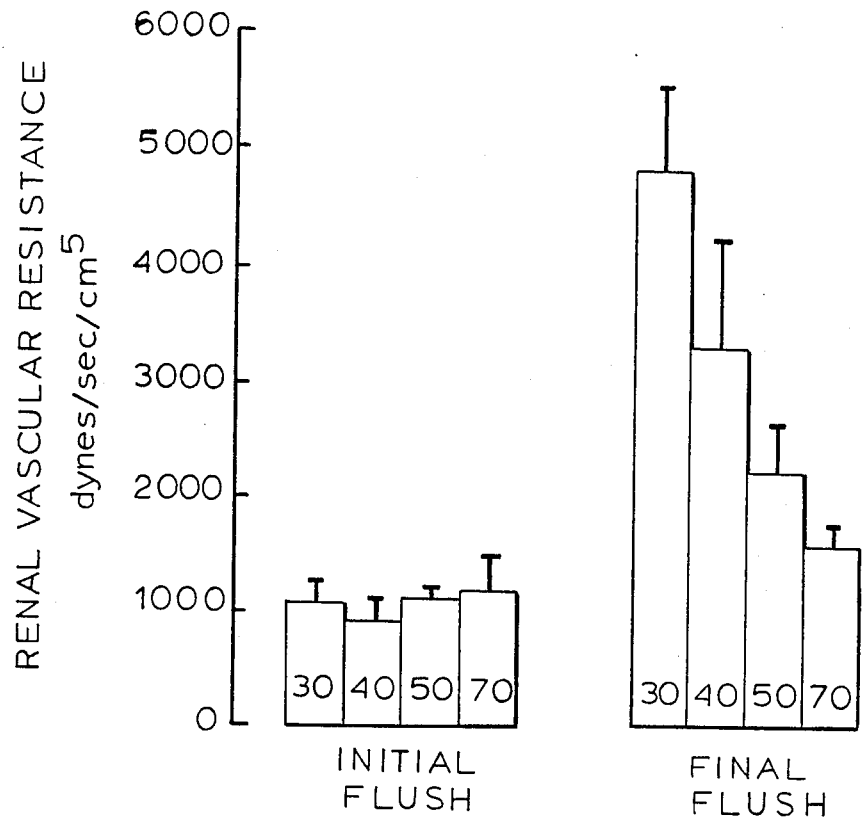
_Fig. 8_
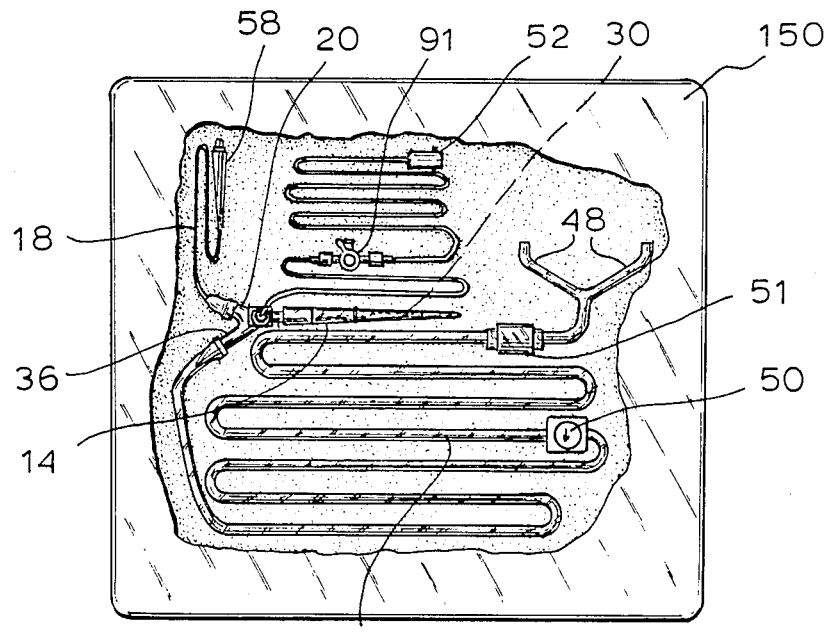
_Fig. 9_

APPARATUS AND METHOD FOR MULTIPLE ORGAN PROCUREMENT

BACKGROUND OF THE INVENTION

The present invention relates to the art of internal organ transplant and, in particular, to techniques for removal of such organs from the body.

Recent success in transplantation of internal human organs such as the liver, pancreas, heart, kidney, etc. has lead to efforts directed toward maximum utilization of donors. Increasing the population of donors as well as multiple organ retrieval from a single donor have both been contemplated as ways to increase available organs. For example, it has been reported that in one country, the Netherlands, the annual occurrence of end-stage renal disease is 50/million population, while the donor population is only 26/million. Ruers, et al. "Non-Heart-Beating Donors: A Successful Contribution to Organ Procurement," *Organ Procurement II Proceedings of the Second International Congress on Organ Procurement* Oct. 3-5, 1985, Detroit, Mich., ppg. 28-30 (1986). In order to overcome this problem, Ruers, et al. have suggested that non-heart-beating donors who experience sudden circulatory arrest in an uncontrolled situation be accepted as donor candidates for kidney transplants.

Additionally, multiple organ procurement from a single donor would help alleviate the shortage of internal organs available for transplantation. Thus, in a procedure where a human heart or liver is removed, the kidneys (and/or the liver when the heart is first removed) can also be used to increase the number of available organs.

Problems incurred during organ transplantation relating to irreversible damage due to lack of blood supply in an organ or tissue, i.e., ischemia, are particularly troublesome in those procedures where a delay is experienced between cessation of spontaneous circulation and organ removal (whether occasioned because of uncontrolled conditions or multiple organ procurement procedures). Accordingly, traditional removal techniques, which include ex vivo flushing with a cold solution while the organ is immersed in, for example, a vessel filled with an ice-slush, have been enhanced by in situ preservation of the organ(s). Preservation techniques must be initiated in the uncontrolled situation immediately upon cessation of cardiac activity and continued until removal. Similarly in multiple organ procurement, in situ preservation must be maintained from cessation of spontaneous circulation until removal.

A technique known in the art is to simultaneously flush and cool the organ(s) in situ, whereby the oxygen demand of the organ can be reduced while cleansing the organ. One device known in the art for in situ flush cooling is a double balloon triple lumen catheter, which can be inserted into the common iliac artery and aorta. A lower balloon is inflated and the catheter pulled back until the lower balloon is seated at the aortic bifurcation, at which point the upper balloon is inflated. When both balloons are inflated, hopefully that part of the aorta is isolated where the circulatory conduits leading to the visceral organs, especially the renal arteries, are located. In view of the fixed nature of the occlusive balloons in the double balloon triple lumen catheter, there exists the possibility of failing to correctly isolate the appropriate segment of the aorta. Furthermore, the fixed nature of the balloons may require different sizes. Finally, the fixed double balloon configuration minimizes the flexibility to isolate selected segments of the aortic passage for introduction of flush solution.

In addition to the drawbacks set forth above with regard to the use of the double balloon triple lumen catheter, observed in non-heart-beating donors, other deficiencies have recently been observed in in situ flush cooling which suggest that kidneys, for example, are poorly flushed and cooled. Consequently, it has been deemed appropriate to identify as a standard those flush cooling requirements, such as volumetric flow and pressure as they relate to cooling, and the technique(s) necessary to effect proper organ procurement for purposes of regaining viability after transplantation.

Thus, it is an object of the present invention to provide a device and method for isolating the internal visceral organs for multiple organ procurement.

Another object of the present invention is to provide a device in which adequate flush and cooling of visceral organs can be effected in situ in order to preserve multiple visceral organ(s) for transplantation.

Other objects will be made known to the skilled artisan in view of the following disclosure.

SUMMARY OF THE INVENTION

The present invention includes a method and device for the removal of visceral organs from an animal for purposes of transplantation, such organs having branch connection with the aortic artery. As used herein and in connection with organ removal, "Animal" is to be understood as being inclusive of humans and other species such as canine, primates etc. The procedure for preservation of the organs includes reducing the extent to which such organs are exposed to warm ischemia incident to removal thereof from the animal. The procedure provides the steps of introducing a cannula into a vascular conduit distal to the visceral organs and in fluid communication with the aortic artery, constricting the vascular conduit about the cannula to establish a lower blockage of the conduit, and making a further passage blocking of the aortic artery proximal to the visceral organs to be removed to establish an upper blockage of the aortic artery. A flow of flushing solution is introduced through the cannula into the aortic artery for communication therefrom to the organ being removed. This flow is introduced at a flush pressure (measured at the cannula) required for a given organ, in the case of the kidney, at a pressure at least greater than 30 mm Hg and preferably about 70 mm Hg, and at a flow rate sufficient to provide a renal flush of from about 60 to 70 cc/l00 g/min., such flow being maintained until the core temperature of the organ being removed has been lowered to at least about 22° C. and preferably to about 15° C.

The device provided by the present invention for use in the aforementioned procedure includes in one embodiment thereof, a tapered, beveled tip end cannula received on one of the nipples of a nipple fitting comprised of plural communicatively arranged nipples, with the cannula being insertable in a vascular conduit through an incision therein which is distal the visceral organs, the conduit being in communication with the aortic artery. The tapered shape of the cannula permits insertion of the cannula thru either a femoral or an aortic route thus allowing flush of internal organs without abdominal incision. The cannula also serves for conveniently effecting constricting securement of the conduit about the cannula body in order to establish the lower blockage of the conduit. The device further includes a catheter carrying an inflatable balloon on a tip end thereof, which can be received through a second nipple on the nipple fitting and be extendable through the cannula into the vascular (aortic) artery for positioning the tip end thereof proximal the organ(s) to be removed for which purpose the catheter has length denotive graduations thereon to facilitate accurate blocking positioning of the balloon. The catheter also includes means for connecting same to a source of fluid pressure whereby the balloon can be inflated to establish the upper blockage of the aortic artery. The device also includes a feed tube received on a third of the nipple fitting nipples for communicating a flow of flushing solution from a pressurized source thereof to the cannula for delivery therefrom into the aortic artery and thence to the organs being removed.

The surgeon can preliminarly and if desirable, cut the cannula to a diameter approximating the vascular artery diameter at the incision. The cannula also may include anchoring protuberances thereon employed when securing or anchoring the vascular conduit thereagainst when making the lower blockage. The device also can include means which allows for connection thereof to a pressure monitoring device whereby the pressure of the flushing solution can be monitored during the procedure. Similarly, the feed tube can be provided with an in-circuit solution flow detection means so that continuous monitoring of the flow rate can be made.

As a result of the present invention, a flow of flushing solution can be introduced to visceral organs through the aortic artery at a sufficient pressure and flow rate to effect in situ preservation of the organ for purpose of effecting a safe and efficient transplantation of the organ. Consequentially, donors previously not available for organ transplant such as non-heart-beating donors can be included as well as a method for multiple organ procurement which permits removal of other organs while the in situ preservation techniques are being employed.

For a better understanding of the present invention, together with other and further objects, reference is made to the following description, taken in conjunction with the accompanying drawings, and its scope will be indicated in the claims.

BRIEF DESCRIPTION OF THE DRAWINGS

A fuller understanding of the nature and objects of the invention will be had from the following detailed description taken in conjunction with the accompanying drawings in which:

FIG. 1A is a schematic depiction illustrating the procedure followed when practicing the present invention to effect in situ preservation of the visceral organs of an animal during removal thereof from the animal, the cannula being shown inserted in an incision in the aortic artery at the bifurcation thereof;

FIG. 1B is a schematic depiction similar to FIG. 1A but showing cannula insertion in a femoral artery;

FIG. 2 is a schematic depiction of the device provided by the present invention as same is arranged during an organ removal procedure and showing the feed tube connection to a flushing solution source;

FIG. 3 is side elevational view of the device shown in FIG. 2, portions thereof being broken away for clarity of depiction to facilitate understanding of the constructional character of the device;

FIG. 4 is a top plan view of the device shown in FIG. 3;

FIG. 5 is a horizontal central sectional view of the nipple fitting illustrating the manner in which the nipples formed therein are arranged in common communicative connection one with the others;

FIG. 6 is a plan view of another embodiment of cannula as provided by the present invention and wherein the nipple members through which the catheter balloon is received and the flushing solution is admitted to the cannula are formed as integral appendages on the main cannula body;

FIG. 7 is a fragmentary side elevational view as taken along the line VII—VII in FIG. 6;

FIG. 8 is a graph showing the relationship of Renal Vascular Resistance and Flush pressure; and FIG. 9 is a plan view showing a sterile package containing an in situ organ flushing kit as provided by the present invention.

Throughout the following description like reference numerals are used to denote like parts in the drawings.

DESCRIPTION OF THE PREFERRED EMBODIMENTS

The success or failure of organ transplant depends in large part on minimizing irreversible damage to the organ which decreases the organ's ability to regain full metabolic function upon transplantation. Such damage can occur as a result of Warm Ischemia (W.I.) which is based on unsatisfied metabolic oxygen demand. In the case of kidneys, for example, normal thermic renal oxygen consumption has been shown to be 6.26 ml $O_2$/minute/100 gms kidney weight. The oxygen consumption is reduced, however, by 57% at 30° C. and is further reduced by 90% at 15° C. Thus, it is important to lower the core temperature of the organ to at least about 22°/c but, preferably to about 15° C., in order to reduce its metabolic oxygen demand.

Conventionally, the exposure to damage as a result of Warm Ischemia has been reported as the time interval between cessation of spontaneous circulation and introduction of the flush solution. This concept, however, grossly underestimates the oxygen consumption during the cooling of the organ. Since cooling can be accomplished by several methods, including ex vivo surface cooling, in vivo or in situ cooling, and a combination of in situ and ex vivo cooling, it has been found helpful to refer to the relationship reported by Owen, et al. Owen et al., *Journal of Surgical Research*, Vol. 27, pg. 100 (1979) regarding oxygen consumption during cooling which can be expressed in minutes of Warm Ischemia (W.I.):

$$W.I. = 0.23 \frac{\ln 38}{38 - T} + \frac{0.08 \, t^2}{t_{\frac{1}{2}}}$$

wherein T=final core temperature (C°), t=flush time (i.e., time from initiating flush flow until measured final core temperature is achieved) and $t_{\frac{1}{2}}$=time to reduce core temperature by half. Consequently, successful transplantation can to a certain degree be correlated to cooling procedures which provide acceptable warm ischemia times.

Thus extensive experimentation has been conducted using kidneys of dogs weighing 50–60 lbs. In each of the tests, measurements were taken of the pressure of the flush fluid being administered (mm Hg), the rate of flow of the flush fluid (cc/min), the core temperature of the organs (°C.), the renal blood flow (RBF) to the kidney (cc/gram/min), after reperfusion and in some cases the resistance of the kidney to flush flow (RVR) was measured (dynes/seconds/centimeters). The flush solution in all cases was Collins ® solution (a product of Baxter-Travenol) with a small amount of Trifluoroperazine (TFP), introduced at a temperature of about 4°–8° C.

The kidneys harvested pursuant to the experiments were (1) flushed ex vivo while immersed in ice; (2) some were flushed in situ at various pressures and were subjected to subsequent surface cooling before reperfusion; and (3) some were flushed in situ and reperfused without a subsequent surface cooling in ice.

The data set forth below in TABLE I correlates the resultant renal blood flow (RBF) after transplantation to the flush pressure and calculated Warm Ischemia (W.I.) time.

TABLE I

|  | Run Designation | No. of Kidneys | Flush Pressure (mm Hg.) | Surface Cooling (Ice Bath) | Warm Ischemia (Minutes) | RBF After Reperfusion (cc/gram/min) |
|---|---|---|---|---|---|---|
| Pre-Nephrectomy |  | 10 |  |  |  | 2.36 ± .19 |
| Ex Vivo | A | 6 | 70 | Yes | — | 2.01 ± .20 |
|  | *$B_1$ | 4 | 70 | Yes | 1.57 | 1.76 ± .19 |
|  | *$B_2$ | 4 | 30 | Yes | 1.90 | 1.66 ± .11 |
| In Situ | *$C_1$ | 4 | 30 | Yes | 1.90 | 1.58 ± .15 |
|  | *$C_2$ | 4 | 30 | No | 8.50 | 0.61 ± .09 |
|  | D | 6 | 70 | Yes | 0.80 | 2.30 ± .18 |

*The subscript numerals 1 and 2 indicate that the kidneys were right and left kidneys, respectively, which removed from the same 4 animals in each case. It should be noted that extensive studies made by Aryian, et al., Archives of Surgery, Vol. 102, pg 57 (1971), which show that maintenance of renal blood flow of 1.57 cc/gram/minute after transplantation correlating well with organ survival, provided a suitable model for evaluation.

Referring to the results shown in TABLE I, it can be seen that in all cases where the Flush Pressure was maintained at 70 mm Hg, both In Vivo and In Situ, the resulting Warm Ischemia (W.I.) time and Renal Blood Flow (RBF) were found to be at a level which corresponds to a viable transplant. In Situ Flush Pressure of 30 mm Hg without Surface Cooling produced a Warm Ischemia time of 8.50 minutes and a dismal 0.61±0.09 cc/gram/min. flow after reperfusion. This result is of particular significance since the double balloon triple lumen catheter used in clinical procedures produced flush pressures of only 26–42 mm Hg when the flush solution bottle was raised to the ceiling of the operating room.

It is further noted that the In Situ cooling procedures conducted with the device of the present invention in Run D to flush 6 kidneys, when combined with subsequent surface cooling, resulted in an excellent 0.80 minute W.I. time and a post reperfusion RBF of 2.30±0.18 cc/gram/minute.

Further experiments were conducted to demonstrate the relationship between the Renal Vascular Resistance (RVR) and the flush pressure using 28 of the animal kidneys by flushing at pressures of 30, 40, 50 and 70 mm Hg. Changes in the pressure and flush flow were recorded and RVR was assessed. (See FIG. 8). As depicted in FIG. 8, the initial vascular resistance was similar in all 4 groups, e.g., a mean RVR of 1040 dynes/second/centimeter $^5$. After 8 minutes of flush, the RVR of kidneys flush at flush pressure of 70 mm Hg was 1569 dynes/seconds/centimeter $^5$. In contrast, the RVR of kidneys flushed at flush pressure of 30 mm Hg rose dramatically to 4725 dynes/second/centimeter $^5$ with successively smaller rises in the RVR in kidneys at flush pressures of 40 and 50 mm Hg. This data suggests that flush pressures lower than 70 mm Hg result in increase in RVR, progressive decrease in renal flush flow, and ineffective core cooling which can lead to microcirculatory damage, and a decrease in organ viability.

In order to show the validity of the findings and to demonstrate the effectiveness of the device of the present invention a cannula was introduced into the aorta of three dogs (Run No. D) and 3 liters of the cold Collins ® solution were flushed at 70 mm Hg flush pressure resulting in total visceral flush flow of 1100 cc/minute. Core temperatures of 8° C. were achieved within 3 minutes (W.I. time 0.80), and excellent protection of the renal microvasculative was noted after reperfusion (mean RBF of 2.3 cc/gram/minute). Thus, it has been very clearly shown that quick and efficient cooling of an organ to be removed for transplant is very important and can even be critical to viability.

Furthermore, in addition to these experiments conducted on dogs it has been demonstrated on 10 human donors that the present claimed device and method can be effectively used in in situ preservation of the organ after cessation of circulation, thus providing additional organ source from non-heart-beating donors as well as from multiple organ donors.

Referring now to FIG. 1A, there is schematically depicted the manner in which organ removal procedure can be carried out, e.g., on a human cadaver, employing the method and one form of the device of the present invention. An incision 10 is made in the cadaver vascular conduit 11, in the depicted procedure, at the aortic bifurcation 12 so that cannula 14 (beveled at the tip end as at 27 seen in FIG. 3) extending upwardly from nipple 15 on nipple fitting 16 can be inserted into the aortic artery, a portion of the fore end or tip of the cannula having been cut off prior to insertion so that the cannula inserted portion approximates the artery diameter, such removed portion being shown in long and short dashed lines. About ½ to 1 inch cannula length will extend into the artery. A balloon catheter 18 having balloon 30 and accessed through a second nipple 20 on the nipple fitting is moved upwardly from its position inside the cannula into the aortic artery to a location proximal the visceral organs being removed and in this instance to a point above the location of the artery branch 22 leading to the liver and the respective left and right renal arteries 24, 26 connected to the kidneys, the location positioning of the balloon for proper blocking being externally determined by reference to graduations 7 on the catheter which enable the surgeon the ascertain that the balloon is situate where desired.

Pressurized fluid is then communicated as by hypodermic syringe connected to catheter 18, through the catheter to inflate balloon 30 and thus establish an upper aortic artery blockage. Lower blockage of the aortic artery is effected as at 32 by constricting the aortic artery about the cannula as with a ligation 34, the purpose being to effect establishment of a lower aortic artery blockage and employing for that purpose the cannula itself as part of the blocking means.

A third nipple 36 on the nipple fitting 16 serves for connection of a feed tube 40 which in turn is connected to a source of a flushing solution disposed some distance remote and elevated from where the transplantation procedure is taking place, the feed tube being held on nipple 36 with a conventional spring clip 41. The flushing solution can be any one of a number of such compositions suitable for such purpose. In general, it will be an aqueous solution containing phosphorus and potassium and to which may be added Trifluoroperazine. Collins ® solution is exemplary of one such solution. In accordance with the invention and to assure that optimal organ flushing is carried out so as to prevent the onset of irreversible ischemia, the flushing solution should be supplied to the organs for at least about 3 to 5 minutes at a certain level of pressure. In the case of the kidneys, the pressure should be one which is in excess of 30 mm Hg but preferably about 70 mm Hg and one which insures a renal flush rate of about 60 to 70 cc/100 g/min.

The flushing solution entering through nipple 36 passes into the cannula whence it is conveyed to the aortic artery and then through the respective artery branches 22, 24, 26 for delivery to the organs involved. Since it is desirable that the flushing be carried out as rapidly as possible and in such manner as to reduce the core temperature of the organs to at least about 22° C. but preferably to about 15° C., the flushing solution, e.g., Collins ® solution supplied in sterile flexible bag containers, is delivered in cold state to the organ, the preferred temperature thereof being in a range about 4° C. to about 8° C. Once the organ has been cooled down to the desired temperature, it can be removed and then maintained under cold preservation conditions in known manner. The invention also provides that flushing of the organs can be effected while maintaining an external cooling of the organs such as by the packing of same in a covering of crushed ice.

In FIG. 1B where the same reference numerals applied in FIG. 1A are used, the entry to the vascular conduit has been made through an incision in the femoral artery 5, a smaller size artery and hence the cannula has not been cut. For convenience of illustration, portions of the device such as the feed tube, nipples and back end of the catheter have not been illustrated, it being understood that they are the same as shown in FIG. 1A.

FIG. 2 illustrates a typical layout of the device and related components as same are used during an a organ transplant procedure, the catheter balloon being deflated, but it being understood of course during the organ transplant procedure the balloon 30 will be inflated in artery blocking configuration. One manner in which a pressurized flow of flushing fluid can be supplied and maintained during the procedure is illustrated wherein the flexible bags 44, 46 containing the flushing solution (kept in cold storage until used) have been elevated a sufficient height to insure a gravity induced pressure flow of sufficient magnitude to insure maintenance of the renal flush rate discussed above although as those skilled in the art will appreciate, pressurized flow from a pump source operating at the pressure levels indicated herein also could be employed in place of gravity flow. The solution bags, 44, 46 are connected to feed tube 40 by Y-branches or feed pieces 48 integral with the tube structure and spring clips 41 maintain the fluid tight connection to the bags. One convenient manner of providing gravity induced flow (desirably at least about 1000 cc/min.) is to suspend the solution bags from a standard in the operating room etc. at a height of about 6 to 8 feet above the operating table, this being a sufficient magnitude of elevation to insure maintenance of a flushing pressure of at least about 70 mm Hg, that pressure being the most desired pressure level to employ in the procedure. The pressure could be lower if external organ cooling is employed and it could be higher as well, e.g., up to 90 mm Hg. Continuous monitoring of the flushing pressure and flow rates take place during the procedure and for which purpose an in-line flow indicator means 50 such as one manufactured by American Scientific Products, McGraw, Ill., can be hooked into the feed tube 40. A Bubble Trap 51 also is included in the feed line, being used in conventional manner to vent any air as may have become introduced into the feed tube at the bottle location or in conjunction with making the hookup to the bottles. Such a bubble trap could be included as a component in the kit to be described later and could be identical to the bubble trap embodied in the MOX-100 Renal Preservation Cassette-100-DCM part No. 00124-91 as manufactured by Waters Instruments, Inc., Rochester, Minn. Monitoring of the pressure is readily accomplished by connecting the nipple block interior to a pressure transducer unit 52 of known construction and for example, a pressure transducer of the type as manufactured by Gould Pressure Recording Systems, Cleveland, Ohio and which devices are normally found in a hospital environment. The invention however, provides that a disposable, single use, fully self-contained transducer such as the Gould DTX ® disposable transducer system made by Gould Inc., Cardiovascular Products Division, Oxenard, Calif., could be connected to the feed tube and be included in the kit to be described later. Such monitoring of the pressure and flow rates allows for remedial compensation of any deviation from the desired parameters therefor.

Further description of the device will be given now with continuing reference to FIGS. 3–5. The device in one form thereof includes as noted, nipple fitting 16 which is a transparent, thermoplastic material component have a first nipple 15 which extends longitudinally from one side of the block 16 and on which is fluid-tight mounted cannula 14, the cannula conveniently being made from transparent thermoplastic material and having its widest diameter at the rear end thereof, tapering as shown toward the forward end which is beveled. The cannula can taper from an inside diameter of about 0.5 inch at the rear end to about 0.25 inch at the front end thereof. Converging nipples 20, 36 make entry to the fitting 16 at the other side thereof, and are in communicative connection one with the other as well as with the nipple 15 and as is seen best in FIG. 5. Catheter 18 is provided at its rear end with a tapered barrel segment 58 which has boss 62 thereon for connection of a fluid pressure source device such as a hypodermic syringe for delivery of pressurized fluid (e.g., air) flow through the catheter into the balloon to inflate same, the barrel segment being fitted with a check valve 64 in known manner. Where the balloon catheter passes through nipple 20, a sealing member such as an elastic cuff 68 is received over the nipple to seal same to prevent flushing fluid outflow at that location. Nipple 20 additionally may be provided with a laterally widened flange as at 70 to aid in securement of the cuff thereon and the cuff as will be seen, tightly embraces the catheter where the same passes through.

A ported connector structure in the form of a treaded nipple 80 is carried on top of fitting 16 and receives female cap member 82 of connector tube 84 for connecting the nipple block to the pressure transducer 52, sufficient length of tubing 84 being provided for that purpose. A three way stop cock 91 can be interposed in connector tube 84 to allow, e.g. and depending on orientation of arm 93, communication flow connection to the transducer if arm 93 is in the 12 o'clock position, preliminary procedure of draining blood from the cadaver for tissue typing purposes or injection of dilating agents etc. through tube stub 94 if the arm is in the 3 o'clock position, the arm being shown in a non-operative position of 11 o'clock only for purposes of convenience so that tube stub 94 can be seen. To enhance the fluid tight connections of the cannula 14 and feed tube 40 to the respectively associated nipples 36, 20, these nipples can be provided with radially widened lands 95 so that fluid tight force fit of the cannula and feed tube must be effected when mounting same on the nipple block.

The cannula 14 can be provided with protuberances such as annular bands 92 to serve as an anchorage means when the constriction of the aorta about the cannula is made. The cannula also can be provided with diameter denotive indicia graduations 97 which can be employed if the cannula has to be cut preliminary to insertion in the incision to facilitate proximating the inserted cannula diameter to the artery size since the cannula is intended for use with both adult and child cadavers where aortic and femoral artery sizes differ.

FIGS. 6 and 7 show another form of the device wherein the cannula 114 and nipples 136, 120 are made as a single piece structure, eliminating the need for a fitting block. Ported connector 180 also can be made as part of the cannula structure, the cap member 182 which is mounted on connector 180 not being shown in FIG. 7. Other modified forms of the device could be made within the scope of the disclosed invention, for example, a cannula could be made with a side wall slot near the rear end through which the balloon catheter could be received. A suitable flexible seal could be fixed to the cannula to cover the slot except for catheter pass through. The rear end of the cannula could serve as the connection point for the feed tube.

As shown in FIG. 9, the component parts of the device designated with the same reference numerals as previously used, can be provided in a sterile kit of such components, being housed within the sterile environment of sealed package 150. Within the kit are all of the components in assembled form needed (except for flushing solution, and balloon inflation syringe) for use in an operating room or such other site such as an ambulance where cadaver organ transplantation is to be made. In dealing with a transplantation opportunity the surgeon is not always given lengthy advance notice that a donor cadaver is available for such purpose. Since the carrying out of that procedure requires ready availability of the device components, it is salutary that they be found in one convenient package as the surgeon will have little time to seek any component that is not immediately at hand. For example, the feed tube 40 which desirably and in conjunction with the flow a rate requirements of the procedure, should be a flexible tube length with an inside diameter of about 9.5 mm and a total length in excess of 3 meters so that the solution bags (a non-sterile component) not only can be elevated for pressure purposes but can be kept remote from the sterile zone where the procedure is being carried out, is a component not always found in an operating room. Similarly, a bubble trap 51 may not be readily available. Accordingly, the kit provides all the vital components needed to carry out the procedure and which otherwise might be wanting in a given procedure location. The components in the kit and all of which have been earlier described are arranged in the compact array shown in FIG. 9.

While there has been disclosed above only certain embodiments of method and device of the present invention, it will be appreciated that various modification can be made thereto by those skilled in the art without departing from the inventive concept disclosed.

What is claimed is:

1. In a method for the removal of visceral organs from an animal for transplant purposes, such organs having branched connection with the aortic artery, a procedure for in situ preservation of the organs by reducing the extent to which the organs are exposed to Warm Ischemia incident to removal from the animal, the procedure including the steps of
    introducing a cannula into the a vascular conduit through an incision made in said conduit distal the visceral organs and in fluid communication with the aortic artery, securing the vascular conduit against and about the cannula proximal the incision to therewith establish a lower blockage of such conduit,
    passage blocking the aortic artery proximal the visceral organs to be removed to establish an upper blockage of the aortic artery, and
    introducing a flow of a flushing solution through the cannula into the vascular conduit and thence the aortic artery for communication therefrom to the organs being removed and at a
    a. pressure of at least greater than 30 mm Hg., and
    b. a flow rate sufficient to provide a renal flush of about 60 to 70 cc/100 g/min., and maintaining such flow until the core temperature of the organs being removed has been lowered to at least about 22° C.

2. The method of claim 1 in which the solution pressure and flow rate are continuously monitored during the procedure to allow for compensation of any deviation from the required levels thereof.

3. The method of claim 1 further comprising surface cooling the organs during the time same are being flushed.

4. The method of claim 3 in which the surface cooling is effected with an ice covering of the organs.

5. The method of claim 1 in which the upper blockage of the aortic artery is effected with a balloon catheter accessed through the cannula.

6. The method of claim 1 in which the flushing solution flow rate is maintained at least about 1000 cc/min.

7. The method of claim 1 in which the cannula is inserted into the vascular conduit at the aortic bifurcation.

8. The method of claim 1 in which the cannula is inserted into the vascular conduit at a femoral artery.

9. The method of claim 1 in which the flushing solution pressure is in the range greater than 30 mm Hg. to 90 mm Hg.

10. The method of claim 9 in which the flushing solution pressure is at least about 70 mm Hg.

11. The method of claim 1 in which the flushing solution is introduced into the vascular conduit at a temperature of about 4° C. to about 8° C.

12. The method of claim 1 in which the flushing solution contains potassium and phosphorus.

13. The method of claim 12 in which the flushing solution additionally contains Trifluoroperazine.

14. The method of claim 1 in which the flushing solution flow is maintained for a period of at least about 3 to 5 minutes.

15. The method of claim 1 in which the pressurized flow of flushing fluid is a gravity induced pressure flow.

16. The method of claim 1 in inch the flushing solution flow is maintained until the core temperature of the organs being removed has been lowered to at least about 15° C.

17. Device for employment in the removal of visceral organs from an animal for transplant purposes, the device being used for flushing of such organs in situ with a flush solution flow communicated thereto from the aortic artery, the device comprising a cannula which can be inserted in a vascular conduit through an incision made in said conduit at a location distal said visceral organs and in fluid communication with the aortic artery, and with sufficient insertion distance so that the vascular conduit can be secured against and about the cannula proximal the incision to therewith establish a lower blockage of said conduit, said cannula further having a pair of nipples connected thereto proximal one end thereof and each communicating with the interior of the cannula, a catheter carrying an inflatable balloon received through one of said nipples and extendible through said cannula into said vascular conduit for positioning the inflatable balloon proximal the organs to be removed, said catheter including means for connecting same to a source of fluid pressure whereby said balloon can be inflated to establish an upper blockage of the aortic artery, and a feed tube received on the other of said nipples for communicating a pressurized flow of flushing solution from a source thereof to said cannula for delivery therefrom into said vascular conduit and thence to said organs, there being sealing means associated with the first nipple to prevent ooutflow of flushing solution therefrom, the catheter having leakage excluding passage through said sealing means.

18. The device of claim 17 in which said cannula includes constriction anchoring protuberance means thereon remote from the said one end thereof.

19. The device of claim 17 in which the cannula has an inside diameter of about one-half inch at the said one end thereof.

20. The device of claim 19 in which said cannula tapers to narrower dimension in the direction away from the said one end thereof.

21. The device of claim 20 in which the cannula tapers to a smallest inside diameter of about one-quarter inch.

22. The device of claim 17 further comprising a ported connector means in communication with said cannula and receptive of a tube for communicating said cannula interior location to a pressure monitoring device.

23. The device of claim 17 in which said feed tube has sufficient length to communicate flushing solution from a source thereof elevated above said cannula a height effective to provide a gravity induced solution pressure in the aortic artery of greater than 30 mm Hg and up to 90 mm Hg.

24. The device of claim 17 in which said feed tube includes mean for connecting an in-line flow meter thereto.

25. The device of claim 17 further comprising a nipple fitting, the cannula being received on a nipple at one side of said fitting, said pair of nipples being connected at another side of said fitting and having common communicative juncture with each other and being in communication with said cannula.

26. The device of claim 17 in which catheter is provided with graduations on the surface thereof for facilitating location placement of the balloon within the vascular conduit.

27. Device for employment in the removal of visceral organs from an animal for transplant purposes, the device being used for flushing of such organs in situ with a flush solution flow communicated thereto from the aortic artery, the device comprising a cannula which can be inserted in a vascular conduit through an incision made in said conduit at a location distal said visceral organs and in fluid communication with the aortic artery, and with sufficient insertion distance so that the vascular conduit can be secured against and about the cannula proximal the incision to therewith establish a lower blockage of said conduit, said cannula further having proximal one end thereof structure defining a pair of conduits each communicating with the interior of the cannula, a catheter carrying an inflatable balloon received through one of conduits and extendible through said cannula into said vascular conduit for positioning the inflatable balloon proximal the organs to be removed, said catheter including means for connecting same to a source of fluid pressure whereby said balloon can be inflated to establish an upper blockage of the aortic artery, and a feed tube received on the other of said conduits for communicating a pressurized flow of flushing solution from a source thereof to said cannula for delivery therefrom into said vascular conduit and thence to said organs.

28. A sterile flushing kit of component parts for providing a flushing circuit for use in maintaining in situ preservation of animal organs during a transplantation procedure wherein pressurized and monitored flow of a flushing solution is delivered to such organs during such procedure, the kit comprising the combination of:

a cannula assembly including a tapered cannula tube having a pair of nipple like branches connected at a rear end thereof, the cannula being insertable along a portion of its front end through an incision into the vascular artery of an animal with said front end presenting structure against and about which the artery can be secured proximal the incision to therewith establish an artery blockage, an elongated catheter having a fore end and a rear end, there being an inflatable balloon carried on the catheter fore end and in communication with the catheter interior, the said balloon and catheter fore end being disposed within said cannula with the remainder length of the catheter extending outwardly from said assembly through one of said branches and such that the said remainder length can be slid back into the assembly to slide the fore end thereof out of the front end of the cannula to position said balloon at a selected blocking position in the animal vascular artery with sufficient of the remainder length being located remote from said second nipple that the catheter rear end can be connected with a source of pressurized fluid to inflate said balloon, there being a flexible cuff mounted on said second nipple with the catheter remainder length having fluid tight sealed passage through said cuff, an elongated flexible feed tube tightly received at one end thereof on the other of said branches, the other end of said feed tube terminating in two feed branch pieces for connecting the feed tube to respective first and second sources of a flushing solution, the feed tube having sufficient length to effect connection of said feed branch pieces at said first and second solution sources when the latter are elevated a distance above said cannula assembly sufficient to provide gravity induced solution pressure at the cannula of at least about 70 mm/Hg, a flow meter in fluid circuit in said feed tube at a location intermediate the ends of said feed tube, said cannula assembly including a ported connector thereon in communication with the interior of said cannula, a flexible connector tube received in fluid tight connection at one end on said ported connector, the other end of said connector tube being adapted for connection to a fluid pressure monitor, and a gas tight envelope enclosing the components aforesaid in sterile enclosure.

29. The kit of claim 28 further comprising a bubble trap in said feed tube spaced closely adjacent the two feed branches thereof.

30. The kit of claim 28 further comprising a pressure monitoring transducer fluid tight connected to the other end of said flexible connector tube.

31. The kit of claim 28 in which said feed tube has a length in excess of 3 meters and an inner diameter of about 9.5 mm.

* * * * *